US00PP08184P

United States Patent [19]

Weinberger

[11] Patent Number: Plant 8,184

[45] Date of Patent: Mar. 23, 1993

[54] APRICOT CV. SUAPRIFIVE

[75] Inventor: John H. Weinberger, Fresno, Calif.

[73] Assignee: Sun World, Inc., Coachella, Calif.

[21] Appl. No.: 772,703

[22] Filed: Oct. 7, 1991

[51] Int. Cl.[5] ..... A01H 5/00

[52] U.S. Cl. ..... Plt./39

[58] Field of Search ..... Plt./39

*Primary Examiner*—James R. Feyrer

*Attorney, Agent, or Firm*—Synnestvedt & Lechner

[57] ABSTRACT

An apricot variety characterized by its early blooming and the early ripening of its fruit that has an elongated large size.

1 Drawing Sheet

This invention relates to the discovery and asexual propagation of a new variety of hybrid apricot *Prunus armenica* cv. Suaprifive. The variety is an early ripening apricot cultivated for the fresh fruit market. It was discovered and first propagated by John H. Weinberger at 5090 E. Church Street, Fresno, Calif., and has as its seed parent the apricot cv. Castlebrite (unpatented). Its pollen parent is not known as fertilization was accomplished by open pollination of the seed parent and budding the selected chance seedling to Nemaguard rootstock.

The new variety cv. Suaprifive may be distinguished from other presently available commercial apricot cultivars by the following combination of characteristics: Suaprifive blooms earlier than most apricot cultivars and is also distinguished by its early ripening, its elongated shape and its large size. The new variety maintains these distinguishing characteristics through successive asexual propagations by, for example, budding.

Among the characteristics which distinguish the new variety of apricot tree from its seed parent, Castlebrite may be noted the following: Suaprifive ripens a few days after Castlebrite. Suaprifive is larger, more elongated, blooms earlier and has a more pronounced and deeper suture clef than Castlebrite.

The pollen parent of the new variety is not known.

The accompanying drawing illustrates, in full color, a typical stem and mature leaves of the new apricot tree and the outer surface ripe fruit as viewed perpendicular to the suture line plane and looking at the suture line. The drawing also illustrates the fruit sectioned in half from end to end, with the stone removed from the flesh.

Throughout this specification, color names beginning with a small letter signify that the name of that color, as used in common speech, is aptly descriptive. Color names with capital letters designate values based upon the R.H.S. Colour Chart, publishedd by The Royal Horticultural Society, London, England.

The descriptive matter which follows pertains to apricots of the new Suaprifive variety grown in the vicinity of Arvin, Kern County, Calif. and is believed to apply to plants of the variety grown under similar conditions of soil and climate elsewhere.

TREE

The tree is of medium size, is of medium vigor, round in shape and hardy. It is drooping in habit. The foliage is of medium density. The trees are productive but uncertain bearers.

The trunk is of medium shape and surface texture. The branches are medium in shape and surface texture.

The branches have a semi-glossy surface appearance and numerous large lenticels.

LEAVES

In general, leaves are of large size, having an average length of about 8.6 cm. and an average width of about 7.1 cm. Leaves are spatulate in outline and upfolded in profile. Leaf blade tips curve downwardly at an acute angle. The serrate leaf margin has a slight undulation. The leaf apex is mucronate; the leaf base is U-shaped. Leaves are of medium thickness.

Leaf color on the upper surface is about Green 137A in color. The upper leaf surface is smooth, with no pubescence and semi-glossy. The lower leaf surface is about Green 137C in color, weak in glossiness with no pubescence. The lower leaf surface is smooth in texture and has a dull surface appearance.

The petiole is of average length and average thickness. There are usually five small-sized globose glands positioned on both the leaf base and the petiole. Glands are about Red-Purple 59A in color. Stipules are deciduous.

Wood (leaf) buds are small size and rounded in shape. Their position, relative to the shoot is adpressed. Leaf bud supports are of medium size and are decurrent.

Leaf buds burst at a very early time for the class.

Anthocyanin coloration of strong intensity is present in flowering shoots. Shoots are average in size and thickness for the class (about 0.7 cm.). Internode length (about 2.5 cm.) and bud density is average for the class. The ratio of wood (leaf) buds to flowering shoots is 1:2.

FLOWERS

Flower buds are hardy in Arvin, Calif., of average size and length for the class. Their shape is plump and positioning is free. There is no pubescence. Flower bud color is about Grayed-Orange 177A.

In Arvin, Calif., flowers attain full bloom, on the average, around the second to third week of February which is early as compared with similar varieties growing in Arvin, Calif. Blooms are of medium duration. Flowers are rosaceous in shape, of medium sized diameter with overlapping petals. The fully opened flower is about Red 56D in color.

The peduncle is of average length and thickness and average in pubescence.

The receptacle is of medium depth and at the white bud stage displays some pubescence on the inner surface and average pubescence on the outer surface.

Sepals do not touch the petals or the receptacle and are ovate in shape, with no pubescence on inner and outer surfaces. Sepals are Red-Purple 59A in color.

None of the flowers display double sepals.

The petals are of average size and transversely broad elliptic in shape. The claw length is short. Margin waviness and base angle are average. Pubescence is absent on both inner and outer surfaces and both surfaces are about Red 56D in color.

The stigma is positioned above the anthers, and the anthers are about Orange Red 30D just before dehiscence.

Pollen is about Yellow 14A in color.

Stamens are perigynously positioned.

There is always one pistil and supplementary pistils are absent.

Ovaries are pubescent and have a medium hair density.

The base of the styles are pubescent and have a medium density of hairs.

FRUIT

The fruit, as described, was ripe on May 10, 1990. The size of fruit at that stage of its development is slightly variable, having an axial diameter of about 5.6 cm. and a transverse diameter in the suture plane of about 5.3 cm. and about 4.8 cm. at a right angle to the suture plane. Fruit varies slightly in form, is unsymmetrical and generally oblong in shape, being compressed laterally toward the suture. The position of the maximum diameter is towards the stem end. The fruit is asymmetric about the suture line. Fruit ripens early in season and is for fresh fruit market use. Keeping quality of the fruit is average and the shipping quality is average. The fruit displays average resistance to insects and diseases.

The suture line is deep and extends from the base to the apex. The depression of the apex on the ventral surface is indistinct. The pistil base does not persist. There is some pubescence of sparse density at the apex.

The stem cavity is circular., about 1 cm. deep, and its breadth about 1.5 cm. The base is oblique. The apex is short and rounded in shape.

The pistil point is oblique in shape.

The stem is of medium length, about 0.8 cm., pubescent, and of average adherence to the stone.

The skin, which is of average thickness and of average texture, shows a slight tendency to crack. Reticulation and roughness of the skin are absent. Skin color is about Yellow-Green 153 D. Down is short and does not roll up when rubbed.

The color of the flesh is about Yellow-Orange 23 C. The amygdalin is wanting and juice is present in moderate amounts. The flesh has a low to medium sugar content. Flesh texture is medium. Fibers are few to average in number and tender. Fruit ripens unevenly to produce fruit of fair eating quality. The flavor is sub-acid, delicate and aroma wanting. The stone/flesh ratio is about 5.3:81.3.

The stone is semi-free, adhering to flesh along both dorsal and ventral edges. The stone retains short fiber-like threads along its ridges. The stone is of large size, about 3.5 cm. in length and about 2.6 cm. in breadth. The width at the stalk end of the stone is about 0.4 cm. and about 1.4 cm. in thickness. The angle of the stalk end is obtuse. The form of the stone in profile is generally ovoid and in ventral view is flattened. The stone's base is straight and its apex is nearly rounded. The hilum is oblong. The position of the stone's maximum breadth is toward the middle and the sides are generally equal. The surface of the stone is pitted throughout. An outgrowing keel is well developed. The ridges are jagged. The pits are angular. The ventral stone edge is thin and winged throughout. The dorsal stone edge is average. The stone is about Grayed-Orange 165A. There is no tendency to split.

What is claimed is:

1. A new variety of apricot cv. Suaprifive as illustrated and described.

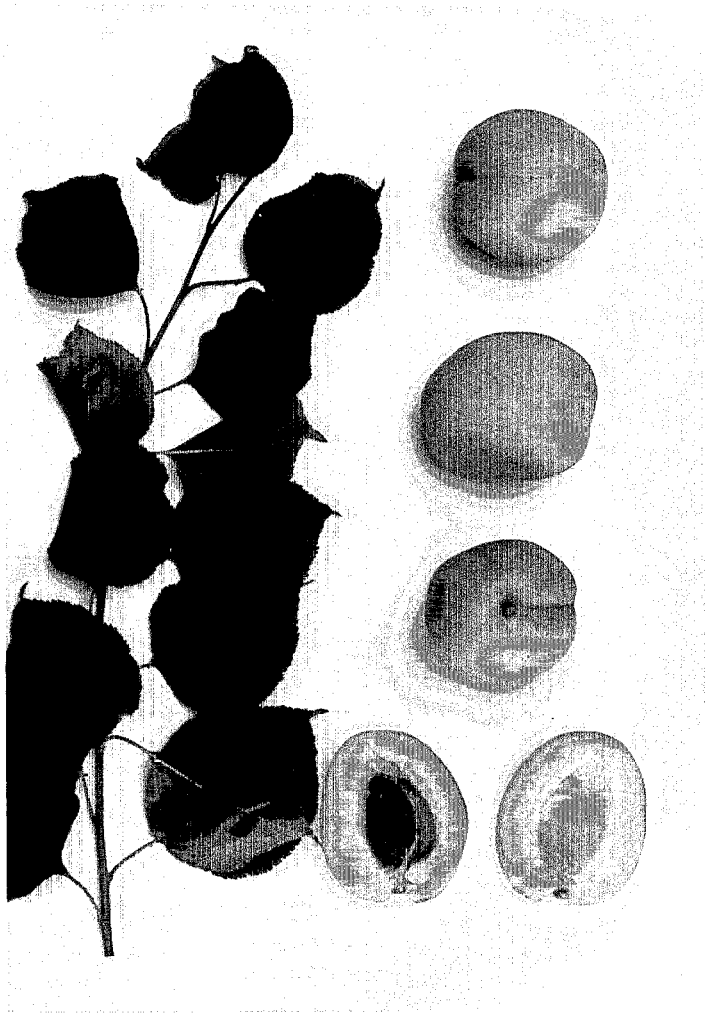

* * * * *